US010016626B2

(12) United States Patent
Zovrin et al.

(10) Patent No.: US 10,016,626 B2
(45) Date of Patent: Jul. 10, 2018

(54) COSMETIC TREATMENT DEVICE AND METHOD (71) Applicant: LUMENIS LTD., Yokneam Ilit (IL)

(72) Inventors: Boaz Zovrin, Yokneam Ilit (IL); Yoram Eshel, Yokneam Ilit (IL); Yacov Domankevitz, Zichron Yaacov (IL); Yoni Iger, Yokneam Ilit (IL)

(73) Assignee: LUMENIS LTD., Yokneam (IL)

( * ) Notice: Subject to any disclaimer, the term of this patent is extended or adjusted under 35 U.S.C. 154(b) by 197 days.

(21) Appl. No.: 15/089,638

(22) Filed: Apr. 4, 2016

(65) Prior Publication Data

US 2016/0213952 A1 Jul. 28, 2016

Related U.S. Application Data (63) Continuation of application No. PCT/IB2014/065113, filed on Oct. 7, 2014.

(51) Int. Cl.
*A61N 7/00* (2006.01)
*A61N 1/04* (2006.01)
*A61N 1/32* (2006.01)
*A61B 17/30* (2006.01)
*A61B 18/00* (2006.01)
*A61B 18/14* (2006.01)
*A61N 1/36* (2006.01)

(52) U.S. Cl.
CPC ............ *A61N 7/00* (2013.01); *A61N 1/0456* (2013.01); *A61N 1/0476* (2013.01); *A61N 1/328* (2013.01); *A61B 18/14* (2013.01); *A61B 2017/306* (2013.01); *A61B 2018/00291* (2013.01); *A61B 2018/00464* (2013.01); *A61N 1/36021* (2013.01); *A61N 2007/0008* (2013.01); *A61N 2007/0034* (2013.01); *A61N 2007/0078* (2013.01)

(58) Field of Classification Search
CPC .... A61N 1/0456; A61N 1/0476; A61N 1/328; A61N 1/36021; A61N 2007/0008; A61N 2007/0034; A61N 2007/0078; A61N 7/00; A61B 18/14; A61B 2017/306; A61B 2018/00291; A61B 2018/00464
See application file for complete search history.

(56) References Cited

U.S. PATENT DOCUMENTS

| 6,500,141 B1 | 12/2002 | Irion et al. |
| 2004/0049134 A1 * | 3/2004 | Tosaya ............... A61H 23/0236 601/2 |
| 2007/0255085 A1 | 11/2007 | Kishawi et al. |
| 2009/0171255 A1 | 7/2009 | Rybyanets |
| 2010/0016761 A1 | 1/2010 | Rosenberg |
| 2013/0178764 A1 | 7/2013 | Eckhouse et al. |

FOREIGN PATENT DOCUMENTS

| EP | 2564894 | 3/2013 |
| WO | 20070102161 | 9/2007 |
| WO | 2009013729 | 1/2009 |
| WO | 20110107885 | 9/2011 |

\* cited by examiner

*Primary Examiner* — Ruth S Smith
(74) *Attorney, Agent, or Firm* — ISUS Intellectual Property PLL; A. Jason Mirabito (57) ABSTRACT

A treatment device comprising a cavity to receive body tissue, the cavity comprising a side wall, a closed end wall and an opening to admit tissue, and at least four ultrasonic transducers disposed to transmit ultrasound into the cavity.

10 Claims, 9 Drawing Sheets

COSMETIC TREATMENT DEVICE AND METHOD

RELATED APPLICATIONS

This application is a continuation application of PCT Application Ser. No. PCT/IB2014/065113, filed Oct. 7, 2014, which claims priority to Great Britain Application Ser. No. 1317711.8, filed Oct. 7, 2013.

FIELD OF THE INVENTION

This invention relates to a treatment device, particularly but not exclusively for the treatment of adipose tissue, a treatment apparatus and a method of operating the treatment device.

BACKGROUND OF THE INVENTION

A known aesthetic body shaping technique is the use of ultrasound to treat fat tissue layers below the skin. A problem with known systems is that of directing or concentrating the ultrasonic energy to only affect or treat the desired volume of tissue, i.e. the fat cells, without affecting other regions of the skin. A related problem is that, for ultrasonic transducers, the power transmitted falls away with distance from the transducer. This can be addressed using high-intensity focussed ultrasound, but this is a relatively complex solution. An example of an alternative device is known from US2012/0277587 showing a treatment device which has a cavity into which skin surface tissue is drawn by applying a vacuum. The treatment device comprises two parallel ultrasonic transducers which direct energy into the tissue between them. To provide an effective treatment volume between a pair of transducers however, the power has to be raised sufficiently such that surrounding tissue may be affected and damaged. Circular transducers are also known to provide a strong focal point for the ultrasound but the focal point is relatively small and the transducers are expensive.

SUMMARY OF THE INVENTION

According a first aspect of the invention there is provided a treatment device comprising a cavity to receive body tissue, the cavity comprising a side wall, a closed end wall and an opening to admit tissue, and at least four ultrasonic transducers disposed to transmit ultrasound into the cavity.

The ultrasonic transducers may be disposed such that the beams generated by the transducers overlap to define a treatment volume within the cavity.

The treatment volume may be spaced from the end wall.

The plurality of ultrasonic transducers may comprise an opposed pair of ultrasonic transducers.

The treatment device may comprise six ultrasonic transducers arranged in a hexagonal configuration.

The treatment device may comprise three opposed pairs of ultrasonic transducers arranged in a regular hexagonal configuration.

The side wall may comprise internal walls arranged in a hexagonal configuration and the ultrasonic transducers may be disposed within the internal walls.

The treatment device according may comprise a plurality of radio frequency electrodes disposed around the cavity and disposed to transmit radio frequency energy into the cavity The radio frequency electrodes may be disposed in the side wall.

The radio frequency electrodes may be disposed closer to the end wall than the ultrasonic transducers.

The treatment device may comprise tissue engagement means to draw tissue into the cavity.

The tissue engagement means may comprise a connection from the cavity for connection to a low-pressure source.

An auxiliary ultrasonic transducer may be disposed in the end wall of the cavity.

Additional treatment elements comprising light sources may be disposed in the end wall of the cavity.

An auxiliary radiofrequency electrode may be disposed in an upper wall of the cavity.

The treatment device may comprise a TENS electrode to provide pain relief.

According to a second aspect of the invention there is provided a treatment apparatus comprising a treatment device according to any one of the preceding claims and a control apparatus to control the ultrasonic transducers and the radiofrequency electrode.

According to a third aspect of the invention there is provided a method of operating a treatment device according to the first or second aspects of the invention, the method comprising receiving body tissue in the cavity and operating the ultrasonic transducers to transmit ultrasound into the cavity.

The method may comprise operating the ultrasonic transducers with a frequency in the range 200 kHz to 4 MHz, preferably 1 MHz to 3 MHz and most preferably 1.5 to 2.5 MHz, The method may comprise operating the ultrasonic transducers for durations in the range 0.1 seconds to 20 minutes, preferably 0.5 to 10 minutes and most preferably 1 to 6 minutes.

The method may comprise operating the ultrasonic transducers such that the energy transmitted into the tissue is in the range 50 to 700 J cm−3, preferably in the range 75 to 250 J cm−3 and most preferably 100 to 250 J cm−3.

The method may comprise operating the transducers with duty cycle in the range 8 to 100%, preferably in the range 16.6 to 100% and most preferably in the range 33.33 to 100%.

The method may comprise performing a cooling cycle between operation of the ultrasonic transducers.

Where the treatment device comprises RF electrodes, the method may comprise operating the RF electrodes with a frequency in the range 100 to 4000 kHz, preferably 300 to 2000 kHz and most preferably 500 to 1000 kHz.

The method may comprise operating the RF electrodes for durations in the range 10 to 5000 ms, preferably 30 to 2000 ms and most preferably 50 to 750 ms.

The RF power may be in the range 5 to 100 W, preferably in the range 10 to 60 W and most preferably 20 to 40 W.

The method may comprise operating the RF electrodes with a duty cycle in the range 8 to 100%, preferably in the range 16.6 to 100% and most preferably in the range 33.33 to 100%.

Where the treatment device comprises a TENS electrode, the method may further comprise supplying an electrical signal to the TENS electrode.

The method may comprise operating the ultrasonic transducers to generate a generally even energy distribution in body tissue in the cavity.

BRIEF DESCRIPTION OF THE DRAWINGS

Embodiments of the present invention are described by way of example only with reference to the accompanying drawings, wherein.

DETAILED DESCRIPTION OF THE PREFERRED EMBODIMENTS

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated n the drawings. The invention is applicable to other embodiments or of being practiced or carried out in various ways. Also, it is to be understood that the phraseology and terminology employed herein is for the purpose of description and should not be regarded as limiting.

Referring now to FIG. 1 to FIG. 4, a treatment device embodied in the present invention is generally shown at 10. The device comprises a generally toroidal upper element 11, a generally circular lower element 12 and a contact part 13. The upper element 11 and lower element 12 are joined by bolts 14 passing through apertures 15 in the upper element 11 and received in threaded bores 16 in the lower element 12. The contact part 13 is connected to the lower element 12 by screws 17 passing through apertures in an annular outer flange 18 of the contact part 13.

Figure 1:
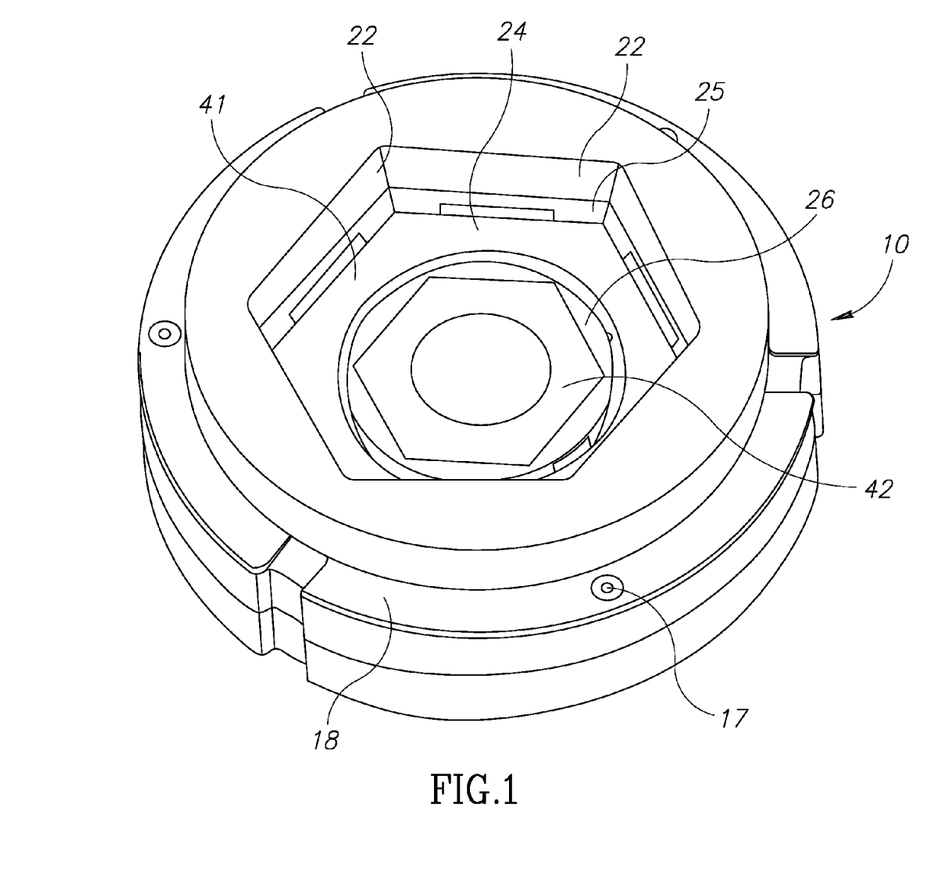
FIG. 1 is a perspective view of the underside of a treatment device embodying the present invention.
Figure 2:
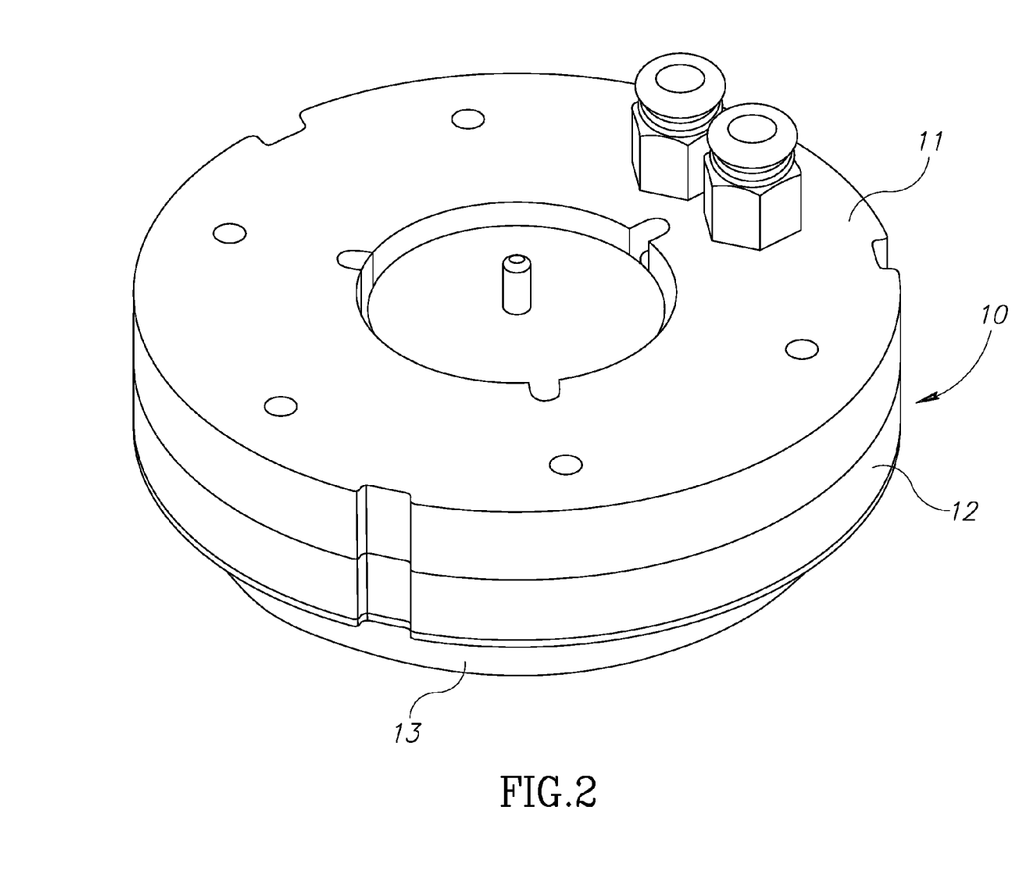
FIG. 2 is a perspective view of the upper side of the device of FIG. 1.
Figure 3:
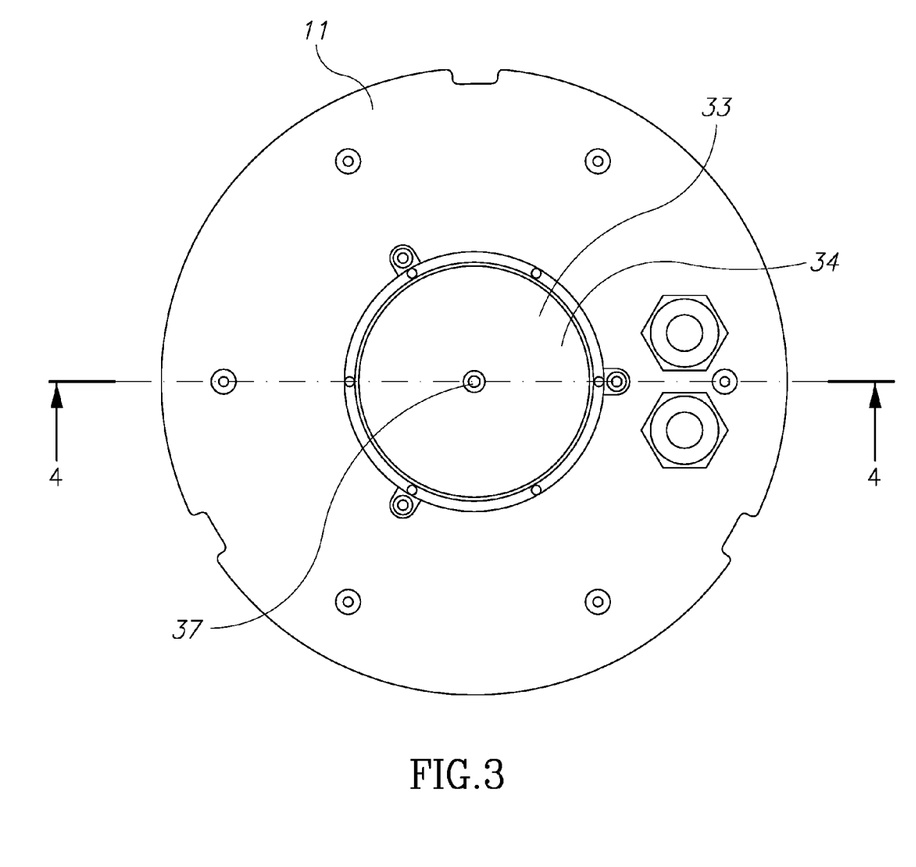
FIG. 3 is a plan view of the top of the device of FIG. 1 and FIG. 2.

The contact part 13 has a generally annular contact surface 20, around the periphery of a cavity 21. The cavity 21 comprises a closed cavity defined by an inwardly directly side wall 22 of the contact part 13 which extends perpendicularly or at an angle to the contact surface 20. The closed end wall 23 of the cavity 21 is defined by a shaped surface of the lower element 12. In the present example, the inner face 23 has a generally flat centre surface 24 joined to the wall 22 by angled surfaces 25. As best seen in FIG. 1, a central portion 26 of the flat face 24 is formed as a circular recess. In this example the side wall 22 is generally hexagonal and made of six internal walls, defining a cavity 21 which is a regular hexagon A tissue engagement means is generally shown at 30 to draw tissue into the cavity 21. In the present example, this is performed by suction. A central part of the lower element 12 defines a vacuum distribution chamber 31, the distribution chamber having annular upstanding wall 32. The chamber 31 is in flow communication with the cavity 21 through channels 31a. The upper surface of the distribution chamber 31 is closed by a cap part 33. The cap part 33 comprises a planar element 34 with annular wall 35 extending around the periphery. The dimensions of the planar element 34 and annular walls 35 are such that when the cap 33 is in position, the annular wall 35 engages the outer surface of the upstanding wall 32. Seals 36 ensure a sealing engagement between the annular wall 35 and upstanding wall 32. A connection nipple 37 is mounted on the cap 33 with a channel 38 extending therethrough to enable the vacuum distribution chamber 31 to be connected to a vacuum or low pressure source.

Figure 4:
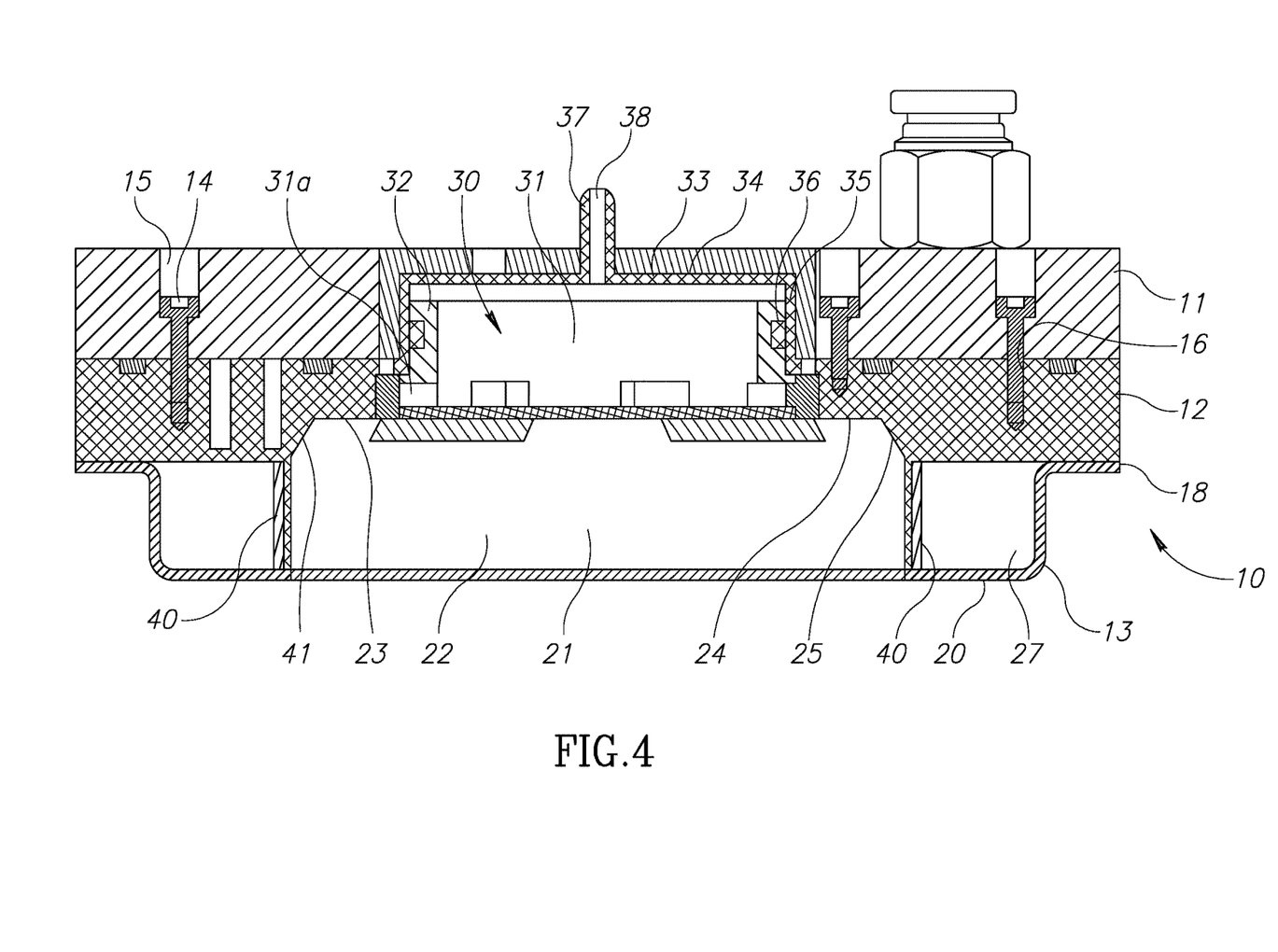
FIG. 4 is a cross-section on line 4-4 of FIG. 3.

To provide for treatment, the treatment device 10 comprises ultrasonic transducers 40 and radiofrequency (RF) electrodes 41. As shown in FIG. 4, the ultrasonic transducers are shown at 40 and are mounted as opposed pairs adjacent the surfaces of the side wall 22 inwardly of the contact surface 20 and spaced from the closed end wall 23. The internal volume 27 of the contact part 13 may be filled with any appropriate material. The ultrasonic transducers 40 may alternatively be mounted elsewhere in the volume 27 and suitably angled as desired. In this example, the ultrasonic transducers comprise flat piezoelectric ultrasonic transducers, each of which generates a generally straight, unfocussed ultrasonic beam in a direction perpendicular to their surface, and hence perpendicular to walls 22 and into the cavity 21.

Radio frequency ("RF") electrodes 41 are similarly mounted on the angled surfaces 35. In the present example, an auxiliary RF electrode is shown at 42 disposed in the recessed area 26 of the flat face 24 of the cavity 21. The RF electrodes 41 are thus offset from the ultrasonic transducers 40, and are located closer to the closed end wall 23.

Figure 5A:
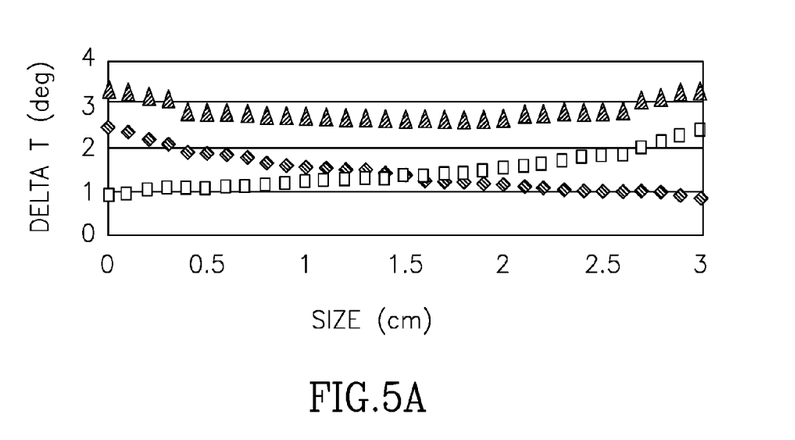
FIG. 5a and FIG. 5b are graphs showing the energy distribution of pairs of opposed ultrasonic transducers.
Figure 5B:
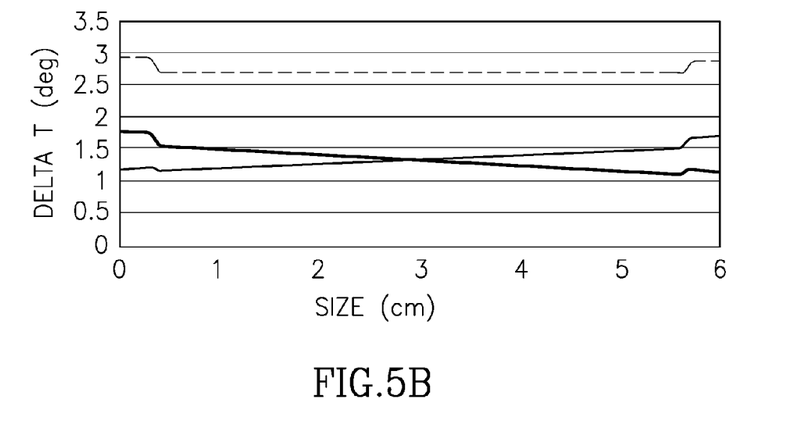

The ultrasonic transducers are preferably mounted in opposed pairs to overcome attenuation of the ultrasonic beams within tissue, as illustrated in the graphs of FIG. 5a and FIG. 5b. The higher the ultrasonic frequency, the greater the attenuation within the tissue. FIG. 5a is a graph showing the transmitted power between two transducers separated by 3 cm, at a frequency of 2 MHz. FIG. 5b shows the transmitted power between two plates separated by 6 cm, at a frequency of 400 kHz. In each case, the power transmitted by the separate plates is shown by red and blue lines, from the right and left respectively, and the attenuation with distance is clearly apparent. The combined power is shown in green, and it is apparent that there is a generally even energy distribution generated in the tissue between the plates. In this way, the treatment occurs across the gap between the two plates. In particular, as the tissue between the plates is heated above the treatment level across the whole of the cavity in an even manner, there is no need to 'overheat' tissue near an ultrasonic transducer to increase the treated area, as would be required by a single transducer.

Figure 6:
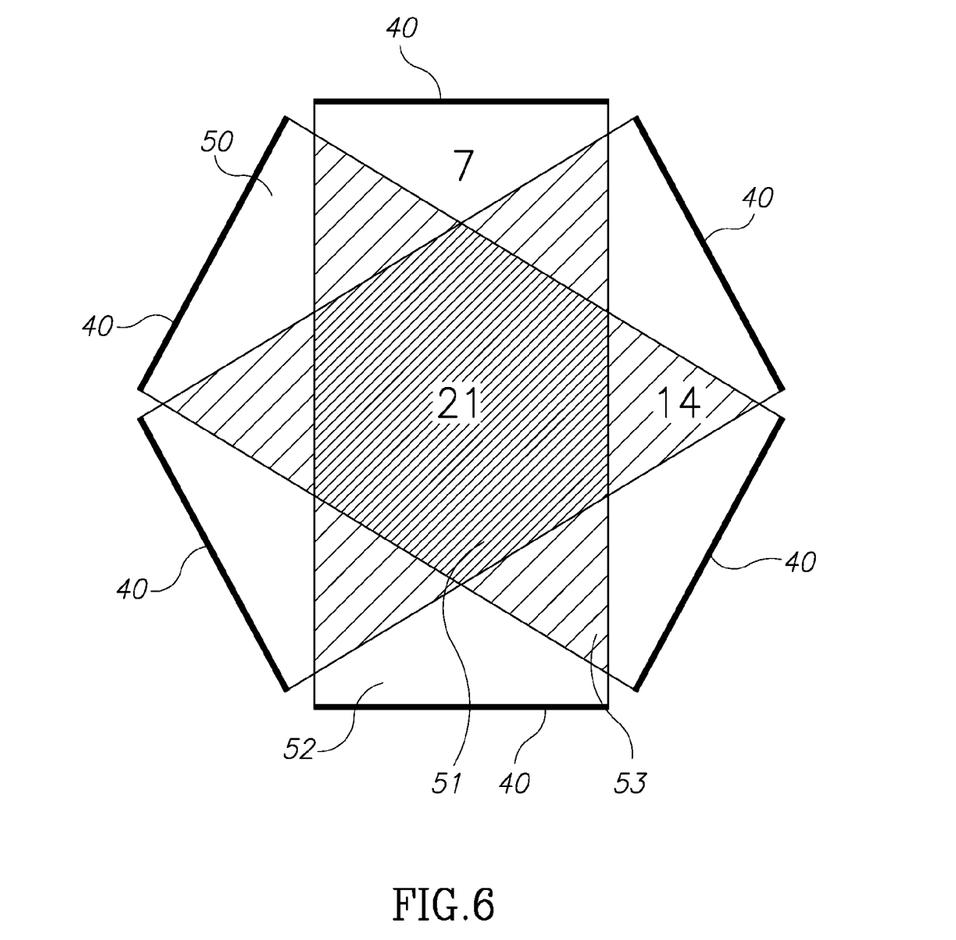
FIG. 6 is a diagrammatic illustration of the ultrasonic beams generated by the device of FIG. 1.

In the present example, where there are 3 pairs of transducers arranged in a hexagonal orientation, the power generated within the cavity is shown diagrammatically in FIG. 6. Opposed ultrasonic transducers 40 each generate a beam generally illustrated at 50. The beams overlap in a central area 51. By selection of the power generated by each of the ultrasonic transducers 40, the temperature elevation in tissue can be controlled such that only tissue within the zone 51 is heated to the required temperature to remove or destroy fat cells or adipose tissue, thus defining a treatment volume. In areas affected by only a single beam 52 or a pair of beams 53, the energy imparted to the tissue is not sufficient to cause damage. At the same time as the ultrasonic transducers 40 are operated to cause fat destruction, the radiofrequency electrodes 41 may be operated to cause tightening in the skin above the treated area of tissue.

Figure 7:
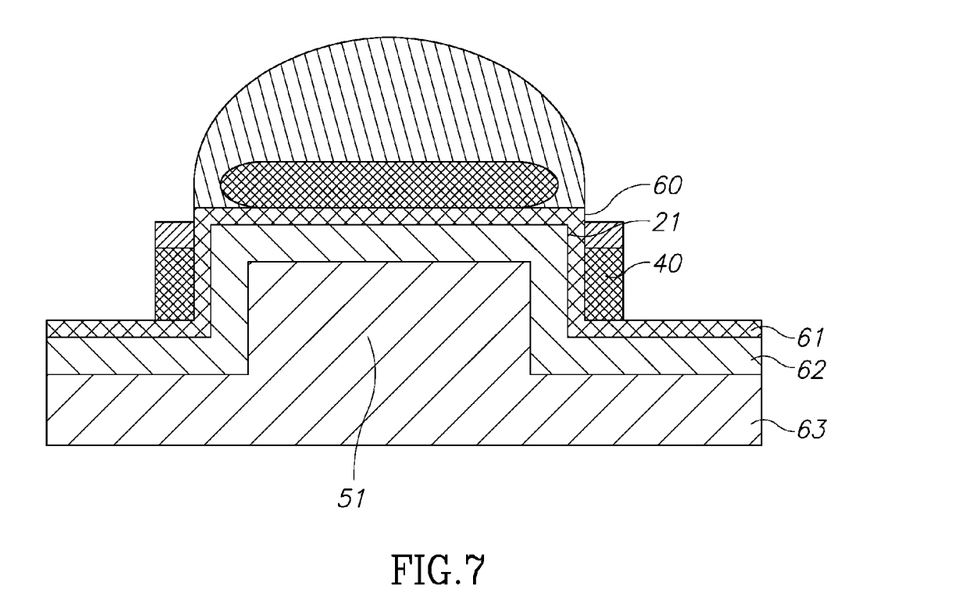
FIG. 7 is a diagrammatic illustration of the device of FIG. 1 in a first mode of operation.
Figure 8:
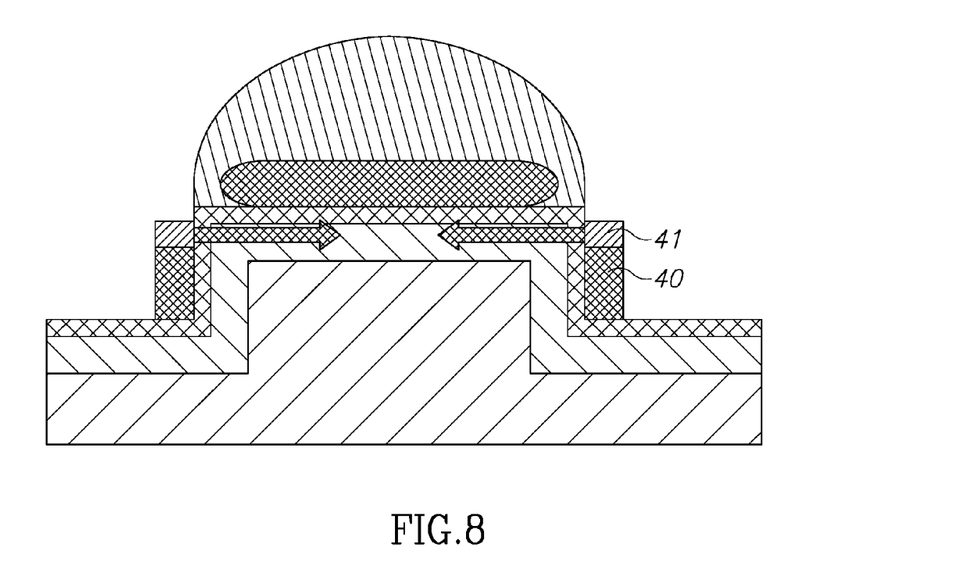
FIG. 8 is a diagrammatic illustration of the device of FIG. 1 in a second mode of operation.

In operation, as illustrated in FIG. 7 and FIG. 8, tissue generally shown at 60 is drawn into the cavity 21 by applying a suitable vacuum to vacuum distribution chamber 31. The side wall 22 can be shaped to optimise contact between the skin and side wall 22. A suitable transmission medium such as a gel can also be applied to the skin. The skin layers in diagrammatic form have an epidermis 61, a dermis 62 and a subdermal layer 63 containing fatty tissue. By drawing the tissue 60 into the cavity 21, as can be seen the fatty tissue 63 is located between the transducers 40, and only that tissue within volume 51 is affected, raising the temperature sufficiently to destroy the fat cells. As illustrated in FIG. 8, the RF electrodes 41 may be simultaneously operated to raise the temperature in the epidermis and dermis to cause skin tightening in known manner. By offsetting the ultrasonic transducers 40 and RF electrodes 41 in this way, different layers of the skin can be treated at once.

Although the hexagonal arrangement of the cavity and ultrasonic transducers as shown herein is advantageous in terms of the volume treated, it is envisaged that other arrangements of the ultrasonic transducers may be used, such that a suitable treatment volume may be defined within the cavity 21 without the disadvantages of requiring local overheating as seen in known devices. For example, four or more transducers 40 may be arranged in a square, pentagonal or heptagonal configuration, or indeed with any number of sides. The polygonal arrangement need not be regular, as in the present example, but may comprise a compressed or irregular polygon depending on the shape and size of the desired treatment volume to be generated by the treatment device.

When included in a treatment apparatus, a suitable controller may be provided to control the ultrasonic transducers 40 and RF electrodes in accordance with an operator's instruction to provide a desired operating regime. The ultrasonic transducers may be operated with a frequency in the range 200 kHz to 4 MHz, preferably 1 MHz to 3 MHz and most preferably 1.5 to 2.5 MHz, for durations in the range 0.1 seconds to 20 minutes, preferably 0.5 to 10 minutes and most preferably 1 to 6 minutes. The energy transmitted into the tissue may be in the range 50 to 700 J cm−3, preferably in the range 75 to 500 J cm−3 and most preferably 100 to 250 J cm−3. The transducers may be operated with duty cycle in the range 8 to 100%, preferably in the range 16.6 to 100% and most preferably in the range 33.33 to 100%.

The ultrasonic transducers may be activated simultaneously or separately. For example, each pair of ultrasonic transducers may be operated in sequence, the duty cycle of each pair of transducers being controlled such that while one transducer pair is active, the other two transducer pairs are in a quiescent part of the duty cycle. Alternatively, individual transducers may be operated in any order, or groups of transducers may be operated together. In a particular cycle of operation, each individual transducer, pair of transducers or group of transducers may be operated once, or may be operated a plurality of times. Similar considerations may apply to the operation of the RF electrodes 41. Accordingly, pairs of RF electrodes may be operated in sequence, the duty cycle of each pair of electrodes being controlled such that while one electrode pair is active, other electrode pairs are in a quiescent part of the duty cycle. It is believed this operation cycle may reduce patient discomfort. However, any other operation cycle may be used, and may be the same as, or different from, the operation cycle of the ultrasonic transducers.

The RF electrodes may be operated with a frequency in the range 100 to 4000 kHz, preferably 300 to 2000 kHz and most preferably 500 to 1000 kHz, for durations in the range 10 to 5000 ms, preferably 30 to 2000 ms and most preferably 50 to 750 ms. The RF power may be in the range 5 to 100 W, preferably in the range 10 to 60 W and most preferably 20 to 40 W. The RF electrodes may be operated with a duty cycle in the range 8 to 100%, preferably in the range 16.6 to 100% and most preferably in the range 33.33 to 100%. The operating parameters may be selected in accordance with the desired treatment or results and the characteristics of the skin or tissue.

Figure 9:
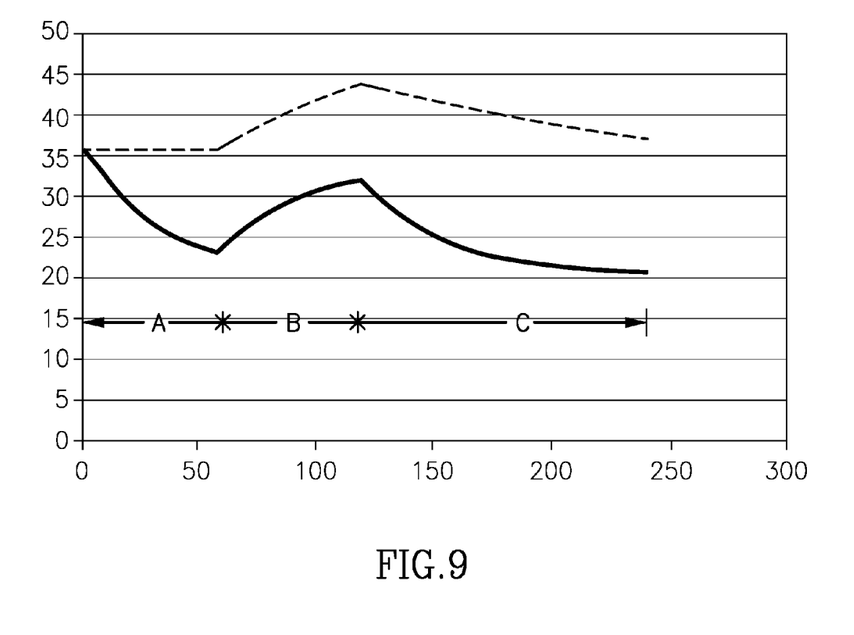
FIG. 9 is a graph showing temperatures of tissue layers during cooling and heating.

The operating regime may include a cooling step as illustrated in FIG. 9. In FIG. 9, the temperature of a fatty subdermal layer (upper line) and skin or dermal layer (lower line) over time are shown. At 0 s, a heating cycle has ended and a cooling period A occurs, in this example 60s. As the fatty subdermal layer is deeper, has a higher thermal capacity and a lower thermal conductivity, it cools at a much slower rate than the dermis. In a subsequent ultrasound heating cycle B, the temperatures of both the dermis and subdermal layer are increased, but because of cooling cycle A, the dermis has a lower starting temperature and is maintained below the temperature at which damage occurs. In contrast, the subdermal layer is raised above a treatment temperature, in this case about 44°. By allowing a further cooling cycle C before beginning heating, it will be apparent that the subdermal layer can be repeatedly treated without causing damage to an overlaying dermal layer.

In the present example, the hexagonal walls 22 are about 30 mm long and enable a volume of 226.1 cm3 to be treated in six minutes, substantially more efficiently than an equivalent high-intensity focused ultrasound device.

Figure 10:
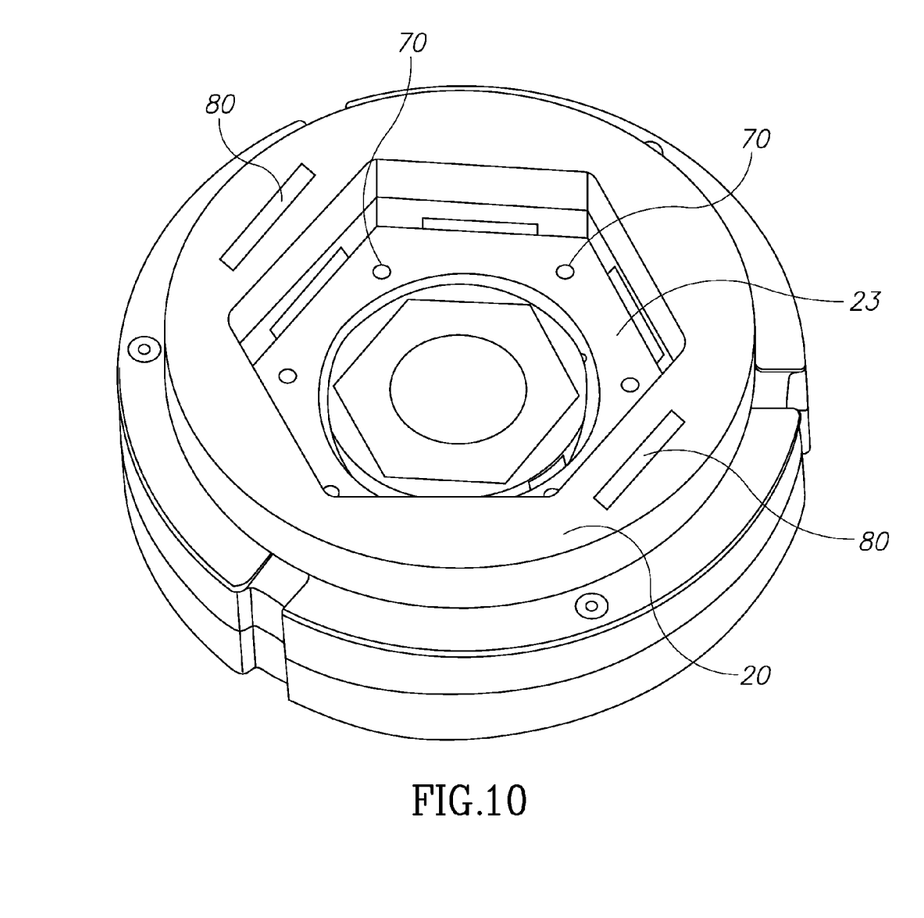
FIG. 10 is a perspective view similar to FIG. 1 showing additional treatment elements.

Further treatment elements are illustrated at 70 and 80 in FIG. 10, although one or both of these elements may be omitted or included as desired.

Elements 70 are disposed on the closed end wall 23, in such a manner that when tissue is drawn into the cavity 21, the elements 70 can treat the skin or dermal layer which is disposed near the elements 70. The elements 70 may be light sources or additional ultrasonic transducers, depending on the type of treatment desired. The energy delivered by the elements 70 may be delivered in a fractional manner, such that energy from each element 70 is delivered into separate, physically spaced locations on the skin, Advantageously, by treating the upper skin layers at the same time or immediately after treating the subdermal tissue layer, a skin tightening effect may be induced over the layers where fat reduction has been performed.

Elements 80 comprise electrodes disposed on the contact surface 20 to perform pain reduction using transcutaneous electrical nerve stimulation (TENS). In TENS, an electrical current is used to stimulate Aβ nerve fibres, associated with touch signals. According to the 'Gate' theory of TENS, the activation of the Aβ nerve fibres causes the activation of inhibitory spinal interneurons. The inhibitory spinal interneurons then block the transmission of information from Aδ and C nerve fibres associated with pain sensation. Consequently, by applying a suitable electrical signal to electrodes 80, a local analgesic effect can be induced, minimising subsequent discomfort caused by the ultrasound treatment.

In the above description, an embodiment is an example or implementation of the invention. The various appearances of "one embodiment", "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Furthermore, it is to be understood that the invention can be carried out or practiced in various ways and that the invention can be implemented in embodiments other than the ones outlined in the description above.

Meanings of technical and scientific terms used herein are to be commonly understood as by one of ordinary skill in the art to which the invention belong, unless otherwise defined.

The invention claimed is:

1. A cosmetic treatment device comprising;
    a cavity to receive body tissue, the cavity comprising a plurality of side walls, a closed end wall and an opening to receive tissue, and six flat piezoelectric ultrasonic transducers disposed to transmit ultrasound into the cavity;
    wherein the plurality of side walls comprise internal walls arranged in a hexagonal configuration and the ultrasonic transducers are disposed within each of the internal walls;
    wherein the ultrasonic transducers when activated, generate a straight ultrasonic beam in a direction perpendicular to the internal walls in the cavity, and are disposed such that the beams generated by the transducers are unfocussed and overlap to define a treatment volume within the cavity;
    further comprising a plurality of radio frequency electrodes disposed within the internal walls of the cavity to transmit radio frequency energy into the cavity;
    wherein the radio frequency electrodes are disposed closer to the end wall than the ultrasonic transducers; and
    further comprising a controller to control the operation of the ultrasonic transducers and the radiofrequency electrodes.

2. The treatment device according to claim 1 comprising a tissue engagement mechanism to draw tissue into the cavity wherein the tissue engagement mechanism comprises a connection from the cavity for connection to a vacuum source.

3. The treatment device according to claim 1 wherein one or more of an auxiliary ultrasonic transducer or light sources or auxiliary radiofrequency sources or a TENS electrode are disposed in the end wall of the cavity.

4. A method of operating the cosmetic treatment device of claim 2 to reduce fat cells and tighten body tissue, the method comprising drawing body tissue into the cavity, the body tissue comprising an upper epidermic layer, a middle dermis layer and a lower layer below the dermis layer including fat cells, the controller causing the ultrasonic transducers to transmit ultrasound into the cavity to reduce fat cells in the dermis layer, and the radiofrequency electrodes to transmit radiofrequency energy into the cavity to tighten body tissue in the epidermis layer.

5. The method according to claim 4 comprising operating the ultrasonic transducers with a frequency in the range of one of: 200 kHz to 4 M Hz, 1 to 3 M Hz and 1.5 to 2.5 M Hz.

6. The method according to claim 4 comprising operating the ultrasonic transducers for durations in the range of one of: 0.1 seconds to 20 minutes, 0.5 to 10 minutes and 1 to 6 minutes.

7. The method according to claim 4 comprising operating the ultrasonic transducers such that the energy transmitted into the tissue is in the range of one of: 50 to 700 J cm$^3$, 75 to 250 J cm$^{-3}$ and 100 to 250 J cm$^{-3}$.

8. The method according to claim 4, the method comprising operating the RF electrodes with a frequency in the range of one of: 100 to 4000 kHz, 300 to 2000 kHz and 500 to 1000 kHz.

9. The method according to claim 4 comprising operating the RF electrodes for durations in the range of one of: 10 to 5000 ms, 30 to 2000 ms and 50 to 750 ms.

10. The method according to claim 4 comprising operating the RF electrodes with an RF power in the range of one of: 5 to 100 W, 10 to 60 W and 20 to 40 W.

* * * * *